(12) United States Patent
Bleicher et al.

(10) Patent No.: US 7,011,960 B2
(45) Date of Patent: Mar. 14, 2006

(54) SUBSTITUTED 2-AMINO-3-(2-AMINO-PHENYLSULFANYL)-PROPIONIC ACIDS

(75) Inventors: Konrad Bleicher, Freiburg (DE); Scott Borthwick, Galashiels (GB); Hans Iding, Rheinfelden (DE); Mark Rogers-Evans, Binningen (CH); Stefan Schmid, Basel (CH); Han Min Tong, Antony (FR); Beat Wirz, Reinach (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 544 days.

(21) Appl. No.: 10/252,971

(22) Filed: Sep. 23, 2002

(65) Prior Publication Data

US 2003/0119152 A1 Jun. 26, 2003

(30) Foreign Application Priority Data

Sep. 25, 2001 (EP) .................................. 01122906

(51) Int. Cl.
| | |
|---|---|
| C12P 13/04 | (2006.01) |
| A61K 38/17 | (2006.01) |
| A01N 43/10 | (2006.01) |
| C07D 291/06 | (2006.01) |
| C07C 323/02 | (2006.01) |

(52) U.S. Cl. .................. 435/106; 514/12; 514/44; 540/491; 560/9

(58) Field of Classification Search ............... 435/106; 514/12, 44; 540/491; 560/9
See application file for complete search history.

(56) References Cited

U.S. PATENT DOCUMENTS 6,420,166 B1 * 7/2002 Iding et al. ................. 435/280

FOREIGN PATENT DOCUMENTS

| DE | 28 04 892 | 8/1978 |
|---|---|---|
| DE | 4009891 | 10/1991 |
| EP | 178 553 | 4/1986 |
| EP | 407 033 | 1/1991 |
| EP | 0 560 408 | 9/1993 |
| EP | 0 577 253 | 1/1994 |

OTHER PUBLICATIONS

Morton et al., Tetrahedron Letters 41, pp. 3029-3033 (2000).

* cited by examiner

Primary Examiner—Ralph Gitomer
Assistant Examiner—Kailash C. Srivastava
(74) Attorney, Agent, or Firm—George W. Johnston; Patricia S. Rocha-Tramaloni; David E. Wildman

(57) ABSTRACT

The present invention relates to a new process for the preparation compounds of formula I

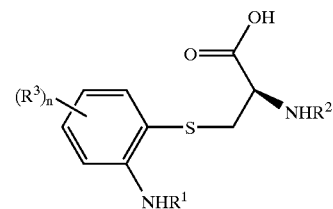

wherein $R^1$, $R^2$, $R^3$ and n are as described in the description which process comprises reacting compounds of formula II

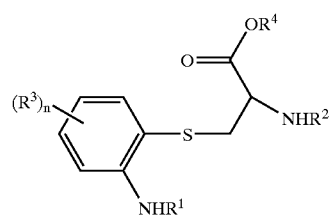

wherein $R^1$, $R^2$, $R^3$, n and $R^4$ are as described in the description, with a protease in an aqueous system containing an organic co-solvent.

The compound of formula I are useful for the preparation of 1,5-benzothiazepines which are useful as enzyme inhibitors, such as protease, interleukin-1β-converting enzyme, elastase or angiotensin converting enzyme, GPCR antagonists (cholecystokinin, angiotensin II receptor).

7 Claims, No Drawings

SUBSTITUTED 2-AMINO-3-(2-AMINO-PHENYLSULFANYL)-PROPIONIC ACIDS

FIELD OF THE INVENTION

This invention is directed to substituted 2-amino-3-(2-amino-phenylsulfanyl)-propionic acids, and a process for preparation of such compounds. These compounds are useful for the preparation of 1,5-benzothiazepines, which are useful as enzyme inhibitors.

BACKGROUND OF THE INVENTION

There have been a number of studies in the art directed to enzymatic stereoselective hydrolysis of racemic mixtures of 2-substituted acids and aromatically substituted L-amino acids, as well as preparation of acids by hydrolyzing esters with enzymes.

EP 0407033 A discloses an enzymatic stereoselective hydrolysis of racemic mixtures of esters of 2-substituted acids, other than 2-halo propionic acids, into the corresponding enantiomeric acids. The reaction is carried out in the presence of *Candida rugosa* lipase isoenzymes, an organic solvent (e.g. toluene) and a reducing agent. The process is especially useful for the stereoselective production of S-ketoprofen, S-ibuprofen, S-fenoprofen, S-2-phenylpropionic acid and S-indoprofen.

EP 0178553 A discloses the preparation of aromatically substituted L-amino acids by selective hydrolysis of the corresponding alkyl esters with chymotrypsin.

DE 2804892 discloses the preparation of optically pure N-acyl-L-threonine by hydrolyzing N-acyl-DL-threonine ester with serine protease, especially subtilisin Carlsberg.

There is believed to be no teaching or suggestion in the art for the preparation of compounds of the formula I using enzymatic reaction.

Attempts to synthesize compounds of the formula

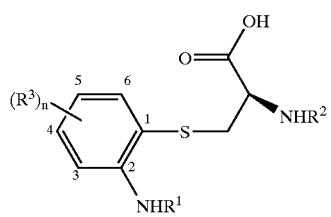

wherein
$R^1$ is hydrogen or alkyl;
$R^2$ is an amino protecting group;
each $R^3$ is independently halogen, carboxyl, alkoxycarbonyl, alkenyloxycarbonyl or benzyloxycarbonyl; and
n is 1 or 2
by chemical hydrolysis have resulted in low yields and decomposition of the starting material.

It is desirable, therefore, to have a novel and inventive process for the preparation of substituted 2-amino-3-(2-amino-phenylsulfanyl)-propionic acids.

SUMMARY OF THE INVENTION

The present invention relates to a new enzymatic process for the preparation of a compound of formula I

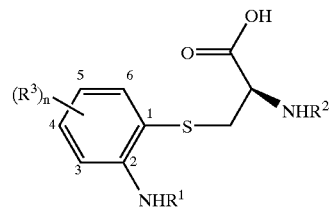

wherein
$R^1$ is hydrogen or alkyl;
$R^2$ is an amino protecting group;
each $R^3$ is independently halogen, carboxyl, alkoxycarbonyl, alkenyloxycarbonyl or benzyloxycarbonyl; and
n is 1 or 2

The compound of formula I was prepared using substituted 2-amino-3-(2-amino-phenylsulfanyl)-propionic acid of formula I

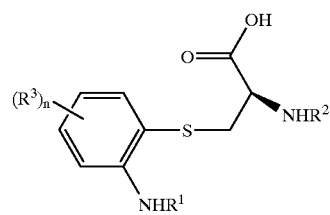

wherein
$R^1$ is hydrogen or alkyl;
$R^2$ is an amino protecting group;
each $R^3$ is independently halogen, carboxyl, alkoxycarbonyl, alkenyloxycarbonyl or benzyloxycarbonyl; and
n is 1 or 2,
which process comprises
reacting compounds of formula II

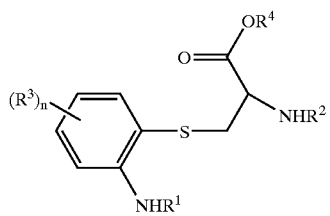

wherein $R^1$, $R^2$, $R^3$ and n are as defined above and $R^4$ is alkyl or benzyl,
with a protease in an aqueous system containing an organic co-solvent.

DETAILED DESCRIPTION OF THE INVENTION

The compounds of formula I are useful for the preparation of 1,5-benzothiazepines, which are useful as enzyme inhibitors, such as protease, interleukin-1β-converting enzymes, elastase or angiotensin-converting enzymes and GPCR antagonists (i.e., cholecystokinin, and angiotensin II receptor).

With the enzymatic approach described herein, a selective hydrolysis reaction of the ester under mild reaction conditions is possible.

In the structural formula presented herein, a solid wedged bond (—◀) denotes that the substituent is above the plane of the paper, and a dashed wedged bond (······III) denotes that the substituent is below the plane of the paper.

The term "alkyl" as used herein denotes an optionally substituted straight or branched chain hydrocarbon residue containing 1 to 12 carbon atoms, such as methyl, ethyl, n-propyl, isopropyl, n-butyl, sec-butyl, isobutyl, tert-butyl, pentyl, hexyl, heptyl, octyl, nonyl, decyl, undecyl, and dodecyl, including their different isomers.

Suitable substituents for the alkyl chain may be selected from 1–3 halogens such as fluorine or chlorine, or $C_{1-4}$-alkoxy such as methoxy or ethoxy. Examples of substituted alkyl are 2-chloroethyl, 2-fluoroethyl, 2,2,2-trifluoroethyl and 2-methoxyethyl.

Alkyl in $R^1$ is as defined above and preferably a straight or branched chain hydrocarbon residue containing 1 to 7 carbon atoms. Alkyl in $R^1$ is more preferably methyl, ethyl, propyl, isopropyl, n-butyl, sec-butyl, isobutyl or tert-butyl.

Alkyl in $R^4$ is as defined above and preferably an optionally substituted straight or branched chain hydrocarbon residue containing 1 to 7 carbon atoms. Suitable substituents for the alkyl chain may be selected from 1–3 halogen, such as fluorine or chlorine, or $C_{1-4}$-alkoxy such as methoxy or ethoxy. Examples of substituted alkyl are 2-chloroethyl, 2-fluoroethyl, 2,2,2-trifluoroethyl or 2-methoxyethyl. Alkyl in $R^4$ is more preferred a straight chain hydrocarbon residue containing 1 to 7 carbon atoms. Examples are methyl, ethyl, propyl, n-butyl, n-pentyl, n-hexyl, and n-heptyl. Preferred examples are methyl, ethyl and propyl. Most preferred alkyl in $R^4$ is methyl.

The term "amino protecting group" as used herein refers to groups such as those employed in peptide chemistry as described in Green T., Protective Groups in Organic Synthesis, Chapter 5, John Wiley and Sons, Inc. (1981), pp. 218–287, such as an allyloxycarbonyl group (ALLOC), a lower alkoxycarbonyl group (e.g., tert-butoxycarbonyl or t-BOC), a substituted lower alkoxycarbonyl group (e.g., trichloroethoxycarbonyl), an optionally substituted aryloxycarbonyl group (e.g., p-nitrobenzyloxycarbonyl, benzyloxycarbonyl (Z) or phenyloxycarbonyl), an alkanoyl group (e.g., formyl, acetyl), an aroyl group (e.g., benzoyl), a halogen-alkanoyl group (e.g., trifluoroacetyl) or a silyl protective group (e.g., tert-butyldimethylsilyl). Preferred amino protecting groups are benzyloxycarbonyl, tert-butoxycarbonyl, allyloxycarbonyl or benzoyl, with the especially preferred amino protecting group being tert-butoxycarbonyl.

The term "alkoxycarbonyl" denotes an $C_{1-7}$-alkoxy residue attached to a carbonyl group (>C=O). Examples of alkoxy groups are methoxy, ethoxy, n-propyloxy, iso-propyloxy, n-butyloxy, 1-sec-butyloxy, iso-butyloxy, tert-butyloxy, pentyloxy, hexyloxy, and heptyloxy, including their different isomers. Examples of alkoxycarbonyl groups are methoxycarbonyl, ethoxycarbonyl, propoxycarbonyl, tert-butoxycarbonyl and the like. Preferred lower alkoxycarbonyl is tert-butoxycarbonyl.

The term "alkenyloxycarbonyl" denotes an alkenyl-oxy residue attached to a carbonyl group (>C=O). The term "alkenyl" as used herein denotes an unsubstituted or substituted hydrocarbon chain radical having from 2 to 8 carbon atoms, preferably from 2 to 4 carbon atoms, and having at least one olefinic double bond, including their different isomers, such as vinyl, allyl and isopropenyl.

Preferred "alkenyloxycarbonyl" for $R^3$ is allyloxycarbonyl or isopropenyloxycarbonyl, and more preferably allyloxycarbonyl.

The term halogen denotes fluorine, chlorine, bromine or iodine. Preferred halogen is bromine.

The number n may be either 1 or 2, preferably the number n is 1.

The substituent $R^3$ may be in any possible position attached to the phenyl ring. If n is 1, $R^3$ may be in the 3, 4, 5 or 6-position of the phenyl ring. Preferably, the $R^3$ substituent is in the 4-position. If n is 2, both $R^3$ substituents may be independent from each other in the 3, 4, 5 or 6-position of the phenyl ring.

A preferred embodiment of the invention is a process for the preparation of compounds of formula I, wherein the compound of formula II is

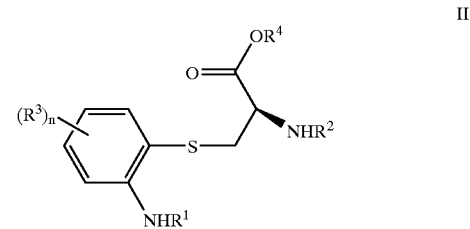

wherein $R^1$, $R^2$, $R^3$, $R^4$ and n are as defined above.

In a further preferred embodiment of the process invention $R^1$ is hydrogen or alkyl, preferably hydrogen;

$R^2$ is an amino protecting group, each $R^3$ is independently halogen, carboxyl or alkenyloxycarbonyl;

$R^4$ is alkyl or benzyl, preferably alkyl; and n is 1 or 2, preferably n is 1.

In another preferred embodiment of the invention, the process is carried out with a protease in an aqueous system, containing an organic co-solvent, at a pH of between about 4.0 to about 10, preferably between 6.0 to about 8.5.

After the enzymatic hydrolysis of the substrate of formula II, the enantiomeric pure product of formula I is separated by acidification and subsequent extraction.

Compound of formula II may be used in any possible mixture of the L or D enantiomers. The conversion is accomplished preferably with a racemic mixture or with a mixture which only contains the L-isomer.

When employing a mixture of isomers, the unreacted remaining D-ester is removed by an extraction step prior to acidification of the reaction medium and subsequent extraction of the L-acid.

Suitable enzymes such as catalysts for the reactions are proteases, preferably cheap bulk proteases of microbial origin, and more preferably *Bacillus* proteases (like Savinase from Novo Nordisk) or subtilisins e.g., subtilisin Carlsberg from Novo Nordisk (Alkalase) or from Solvay (Protease-L) or *Aspergillus* proteases (like Prozyme 6 from Amano) or *Tritachium* proteases (Proteinase K from Fluka).

The most preferred enzyme as catalyst for the reactions is subtilisin Carlsberg (e.g., Alcalase from Novo Nordisk). Alternatively, the enzymes may be used in immobilized form.

The reaction is carried out in an aqueous system with an organic co-solvent, such as a water-immiscible solvent or a water-miscible organic co-solvent. The water-immiscible solvent may be used in any ratio with the aqueous phase, preferably at a ratio of from about 25% to about 75% (v/v). The water-miscible organic co-solvent may be used in an amount as high as tolerated by the enzyme, typically from about 5% to 25% (v/v) but which might exceed even about 50% (v/v), e.g., in case of subtilisin Carlsberg.

The reaction is carried out at a reaction temperature from 0° C. to 50° C., preferably at a reaction temperature between 15° C. and 40° C., and most preferably at a reaction temperature between 15° C. and 25° C.

As to the aqueous phase, common buffer solutions known in the art for biochemical conversions may be used, such as sodium or potassium phosphate in a concentration of up to 1M, preferably between about 5 mM and about 50 mM. Such a buffer solution may additionally contain one of the usual salts like sodium or potassium chloride, and also LiSCN, $Na_2SO_4$ or a polyhydric alcohol, such as a sugar, in a concentration up to 1M.

Suitable organic co-solvents are technically common solvents. Examples are ethers (e.g., tetrahydrofuran (THF), dioxan or tert-butyl methyl ether (TBME)), lower alcohols, esters (e.g., ethyl acetate), and polar aprotic solvents (e.g., dimethylsulfoxide (DMSO), dimethylacetamide, N,N-dimethylformamide (DMF) or acetone). Preferred organic co-solvents are tetrahydrofuran (THF), tert-butyl methyl ether (TBME) and ethyl acetate.

The term "lower alcohol" as used herein denotes straight chain or branched alkyl residues containing 1 to 8 carbon atoms with one hydroxy group, such as methanol, ethanol, propanol, isopropanol, butanol, isobutanol, tert-butanol, pentanol, hexanol, heptanol or octanol, preferably methanol, ethanol, propanol, isopropanol, butanol, isobutanol, tert-butanol and more preferred alcohol are methanol or ethanol.

The substrate is suitably applied as a solution in an about 0.1 to about 25% overall concentration (w/w). A more preferred overall substrate solution concentration is from about 1 to about 10% overall concentration (w/w).

After addition of the enzyme, the pH of the reaction mixture is maintained under vigorous stirring at the selected pH-value by the controlled addition of a base. Preferred bases are aqueous NaOH or KOH solutions.

After termination of the reaction, the enantiomerically pure product of formula I is worked up conventionally after phase separation, by acidification of the aqueous phase with a suitable acid and subsequent extraction with a suitable organic solvent.

Compounds of formula I are synthesized, according to the present invention, in high enantiomeric purity, which means that enantiomeric excesses of about 90% or higher, preferred an enantiomeric excess of about 95% or higher may be achieved.

Compounds of formula II are prepared according to the following reaction scheme or in a conventional manner known to the skilled in the art.

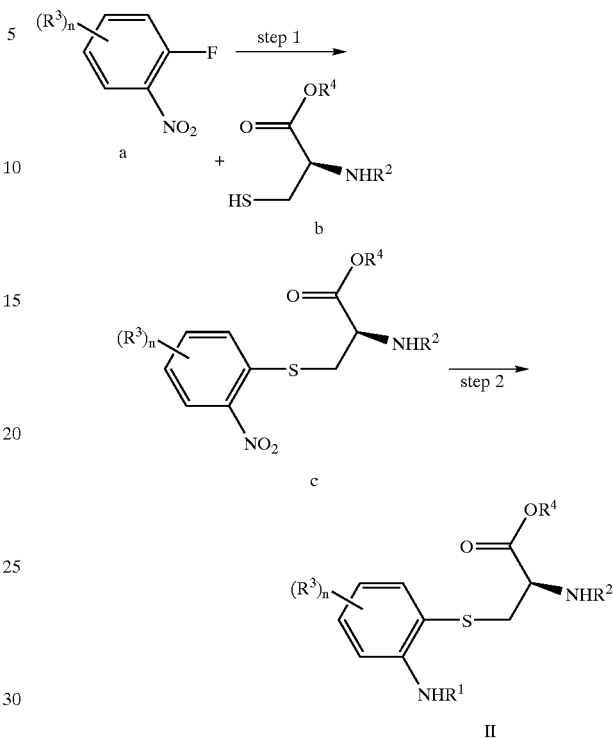

Reaction scheme 1 wherein $R^1$, $R^2$, $R^3$ and $R^4$ are as described for compounds of formula I and II.

In reaction scheme 1, substituted 2-nitro fluoro-aromatic of formula a) is reacted with protected cysteine (e.g. BOC-Cysteine-methylester) of formula b) to obtain the corresponding nitro-phenyl substituted protected cysteine of formula c). The reaction is conveniently carried out under basic conditions (with a diisopropylamine, e.g., ethyldiisopropylamine) in an appropriate organic solvent, such as hexane, diisopropylethyl, ethyl acetate, methanol, ethanol, propanol, dichloromethane, DMF or DMSO. The reaction temperature is preferably between −30° C. to +150° C. More preferably, the reaction is carried out with BOC-Cysteine-methylester in ethanol in the presence of ethyldiisopropylamine at a temperature of 110° C.

Compounds of formula a) and the protected cysteine (e.g. BOC-Cysteine-methylester) of formula b) are commercially available or synthesized according to methods known from textbooks about organic chemistry e.g., from J. March (1992), "Advanced Organic Chemistry: Reactions, Mechanisms, and Structure", 4$^{th}$ ed. John Wiley & Sons).

The second step of the reaction is carried out in that the nitro group of the nitro-phenyl substituted protected cysteine of formula c) is reduced to the corresponding amino-phenyl substituted protected cysteine of formula II. The reduction reaction is carried out according to methods known in the art, for example, known in textbooks on organic chemistry, e.g., J. March (1992), "Advanced Organic Chemistry: Reactions, Mechanisms, and Structure", 4$^{th}$ ed. John Wiley & Sons). The reaction is conveniently carried out with a suitable reducing agent (e.g., Zinc and optional $NH_4Cl$) in acidic media with organic solvents such as hexane, diisopropylether, ethyl acetate, methanol, ethanol, propanol, dichloromethane, DMF, DMSO, preferably methanol. The reaction temperature is preferably between about −30° C. to about +150° C.

The NH$_2$-group of compound of amino-phenyl substituted protected cysteine of formula II may be alkylated with R$_1$X, wherein R$_1$ is as defined above and X is chlorine or bromine.

The compounds of formula II-a and II-b (see below) are novel intermediates and therefore also subject of the present invention

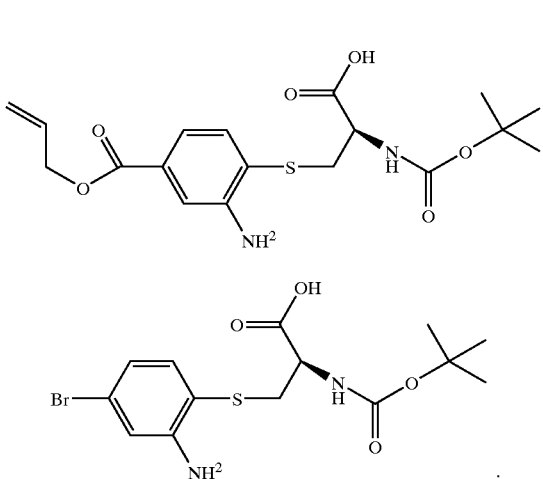

Compounds of the formula I are versatile building blocks for the synthesis of 1,5-benzothiazepines. Such benzothiazepine scaffolds have been used as a constrained dipeptide mimics in various enzyme inhibitors (protease, interleukin-1β-converting enzyme, elastase or angiotensin-converting enzyme), and also as GPCR antagonists (cholecystokinin, angiotensin II receptor). The possible different uses is described in G. C. Morton et al., Tet. Lett., 41 (2000) 3029–3033.

The benzothiazepines are prepared according reaction scheme 2:

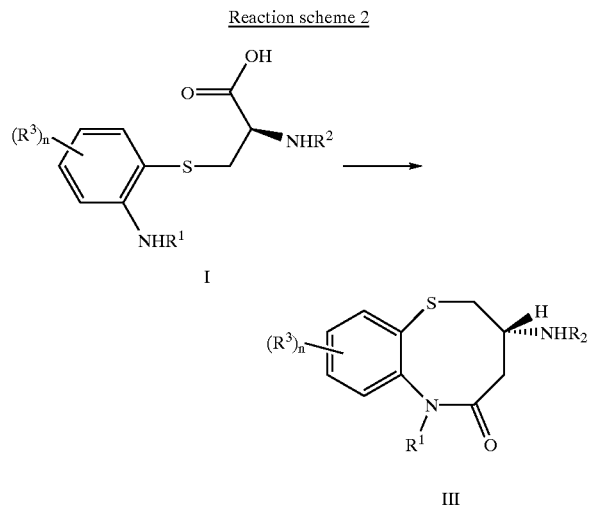

wherein R$^1$, R$^2$, R$^3$, R$^4$ and n are as described for compounds of formula I and II.

The cyclization reaction of compound of formula I to obtain benzothiazepine of formula III is carried out thermally or in the presence of an appropriate reagent, for example as described in G. C. Morton et al., Tet. Lett., 41 (2000) 3029–3033). The reaction is conveniently carried out with a carbodiimide in an appropriate solvent such as hexane, xylene, diisopropylether, ethyl acetate, methanol, ethanol, propanol, dichloromethane, DMF or DMSO. The reaction temperature is preferably between about −30° C. to about +150° C. The reaction is preferably carried out at room temperature in DMF in the presence of EDAC (1-ethyl-3-(3-dimethylaminopropyl)carbodimide hydrochloride).

In the following examples, the abbreviations used herein have the following significations.
ISP-MS means ion spray positive mass spectroscopy;
ISN-MS means ion spray negative mass spectroscopy;
EI-MS means electron impact mass spectroscopy;
SFC means supercritical fluid chromatography;
NMR means nuclear magnetic resonance spectroscopy;
IR means infra red spectroscopy;
HV means high vacuum; and
min means minute(s).

EXAMPLE 1

Preparation of the Starting Material (S)-3-(4-Bromo-2-nitro-phenylsulfanyl)-2-tert-butoxycarbonylamino-propionic acid methyl ester

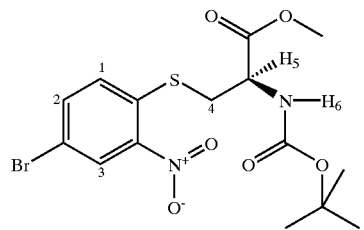

The reaction was carried out as described in M. K. Schwarz et al., J. Org. Chem. 1999, 64, 2219–2231. To a solution of commercially available BOC-Cysteine-Methylester (27.38 g, 116.35 mmol, 1 eq), N-Ethyldiisopropylamine (DIPEA) (4.4 mL, 25.75 mmol, 2.5 eq) in EtOH (310 mL) was added 5-bromo-2-fluoronitrobenzene (25.62 g; 116,45 mmol; 1 eq) and heated at 110° C. for 3 h. The progress of the reaction was monitored by HPLC. The solvent was evaporated to a red-brown oil and this was partitioned between water (600 mL) and ethyl acetate (3×300 mL). Drying (Na$_2$SO$_4$), and evaporation gave crude product which was recrystallised with cyclohexane to give yellow crystals (38.75 g, 77%). Analytical data: $^1$H-NMR (CDCl$_3$, 400 MHz): 1.430 (s, 9H, O(CH$_3$)); 3.350 (dd, 1H, H(4'), J$_{4'-4''}$=5.2 Hz, J$_{4'-5}$=14.4 Hz); 3.500 (dd, 1H, H(4''), J$_{4''-4'}$=5.2 Hz, J$_{4''-5}$=14.4 Hz); 3.755 (s,3H, OCH$_3$); 4.621 (m, 1H, H(5)); 5.301 (d, 1H, H(6), J$_{6-5}$=6.4 Hz ); 7.449 (d, 1H, H(1), J$_{1-2}$=8.8 Hz); 7.670 (dd, 1H, H(2), J$_{1-2}$=8.8 Hz, J$_{2-3}$=2.0 Hz); 8.278 (d, 1H, H(3), J$_{2-3}$=2 Hz). IR: 3353 cm$^{-1}$ (NH); 1765 cm$^{-1}$ (Ester —C=O); 1686 cm$^{-1}$ (Carbamate —C=O); 1546 cm$^{-1}$(Amide —C=O); 1460 and 1329 cm$^{-1}$(NO$_2$); 1220 cm$^{-1}$(Ester). MS: m/z=452.3 [M+NH$_4$$^+$] with $^{79}$Br; m/z=454.3 [M+NH$_4$$^+$] with $^{81}$Br; m/z=457.3

[M+Na$^+$] with $^{79}$Br; m/z=459.3 [M+Na$^+$] with $^{81}$Br. Rf=0.38 in Ethyl acetate/Hexane 1:2 on SiO$_2$.

EXAMPLE 2

(S)-3-(2-Amino-4-bromo-phenylsulfanyl)-2-tert-butoxycarbonylamino-propionic acid methyl ester

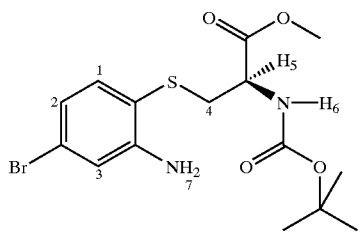

The reaction is carried out as described in J. Slade et.al., J. Med. Chem. 1985, 28, 1517–1521). A mixture of the nitro compound from above (40.34 g, 92.6 mmol, 1 eq), NH$_4$Cl (19.81 g, 370.6 mmol, 4 eq) is added and Zn (79.37 g, 1.204 mmol, 13 eq) in MeOH (950 mL) was heated at reflux for 16 h and the resultant mixture filtered through Celite and washed with boiling MeOH. After concentration, the crude product was partitioned between ethyl acetate and a NaHCO$_3$ (aq.). The resultant oil was chromatographed using ethyl acetate/hexane/3% triethylamine) to give the product (21.11 g, 56%). Analytical data: $^1$H-NMR (CDCl$_3$, 400 MHz): 1.395 (s, 9H, O(CH$_3$)); 3.185 (d, 2H, H(4), J$_{4-5}$=4 Hz); 3.617 (s, 3H, OCH$_3$); 4.446 (s, 2H, H(7)); 4.528 (m, 1H, H(5)); 5.502 (d, 1H, H(6), J$_{6-5}$=8 Hz); 6.793 (dd, 1H, H(3), J$_{3-2}$=2 Hz, J$_{3-1}$=8.4 Hz);6.868 (d, 1H, H(3), J$_{3-2}$=2 Hz), 7.225 (d, 1H, H(1), J$_{1-2}$ =8.4 Hz). IR: 3356 cm$^{-1}$ (—NH$_2$, —NH); 1744 cm$^{-1}$ (Ester —C=O); 1707 cm$^{-1}$ (Carbamate —C=O); 1504 cm$^{-1}$ (Amide); 1250 cm$^{-1}$ (Ester). MS: m/z=405.3 [M+H$^+$] with $^{79}$Br; m/z=407.3 [M+H$^+$] with $^{81}$Br. Rf=0.47 in ethyl acetate/hexane 1:2 on SiO$_2$.

EXAMPLE 3.1

Large Scale Enzymatic Hydrolysis (S)-3-(2-Amino-4-bromo-phenylsulfanyl)-2-tert-butoxycarbonylamino-propionic acid

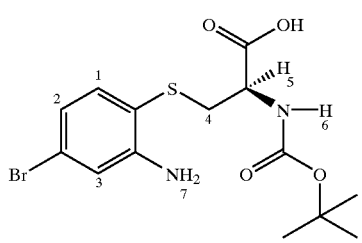

19.9 g (48.02 mmol) of N-tert-butoxycarbonyl-3-(2-amino-4-bromophenylthio)-L-alanine methyl ester (97.8%) was dissolved in 750 ml TBME and emulsified in 3 L buffer solution (0.1M sodium chloride, 20 mM sodium phosphate pH 7.5) under vigorous stirring. 12.0 ml Alcalase 2.4 L and 30 mg Substilisin A [both enzyme preparations are subtilisin Carlsberg from Novo Nordisk] were added and the pH was maintained at 7.5 under vigorous stirring by the controlled addition (pH-static) of 1.0N sodium hydroxide solution. After 7d 44.75 ml of 1.0N sodium hydroxide solution was consumed and the conversion degree was >99% (HPLC analysis). The biphasic reaction mixture was separated. The aqueous phase was washed briefly with 1 L TBME for the separation of small amounts of lipophilic impurities and traces of the remaining substrate. The combined organic phases were extracted with 1×250 ml 0.1 M potassium phosphate buffer pH 7.6. The combined aqueous phases were acidified to pH 2 with 32% hydrochloric acid and extracted with 1.5 L ethyl acetate. The resulting emulsion was separated by the addition of 10% Dicalite under stirring and a subsequent filtration. The aqueous phase was extracted with 2×1 L ethyl acetate. The combined ethyl acetate phases were dried on anhydrous sodium sulfate and evaporated. The residue was dissolved in dichloromethane, evaporated and dried at HV to give 18.79 g N-tert-butoxycarbonyl-3-(2-amino-4-bromophenylthio)-L-alanine as a pale yellow solid (yield: 81.8%). Analytical data: $^1$H-NMR (CDCl$_3$, 400 MHz) 1.399 (s, 9H, OC(CH$_3$)); 3.184 (dd, 1H, SCH$_2$, J=14.2 Hz, J=6.6 Hz); 3.235 (dd, 1H, SCH$_2$, J=14.2 Hz, J=6.6 Hz); 4.515 (m, 1H, COCHNH); 5.517 (d, 1H, CONHCH, J=6.8 Hz); 6.796 (dd, 1H, arom., J=2 Hz, J=8.4 Hz); 6.876 (d, 1H, arom., J=2 Hz); 7.250 (d, 1H, arom., J=8.4 Hz). IR (ATR-IR) 3445 and 3355 cm$^{-1}$ (—NH, —NH$_2$); 2978 and 2929 cm$^{-1}$ broad (—COOH); 1693 cm$^{-1}$ (COOH —C=O, carbamate —C=O); 1508 cm$^{-1}$ (amide —CO—NH); 1247 and 1157 cm$^{-1}$ (COOH). MS (ESI-positive ionization) m/z=391.1 [M+H$^+$] with $^{79}$Br; m/z=393.1 [M+H$^+$] with $^{81}$Br; m/z=413.2 [M+Na$^+$] with $^{79}$Br; m/z=415.2 [M+Na$^+$] with $^{81}$Br. OR [α]$_D$=+53.3° (CHCl$_3$; c=1.0). HPLC analysis: column: ABZ+plus; mobile phase: A: 0.1% TFA in H$_2$0; B: MeCN; gradient B: 30–80% 0–15 min, 80–30% 15–16 min, 30% 16–19.5 min; flow:1 ml/min; pressure: 50–80 bar; detection: UV, 300 nm; retention times: 12.1 min (product-acid) 13.5 min (substrate-ester).

EXAMPLE 3.2

Small Scale Enzymatic Hydrolysis (S)-3-(2-Amino-4-bromo-phenylsulfanyl)-2-tert-butoxycarbonylamino-propionic acid 1.65 g (3.99 mmol) of N-tert-butoxycarbonyl-3-(2-amino-4-bromophenylthio)-L-alanine methyl ester (98%) was dissolved in 65 ml TBME and emulsified in 240 ml buffer solution (0.1M sodium chloride; 20 mM sodium phosphate pH 7.5) under vigorous stirring. 0.75 ml Alcalase 2.4 L [a subtilisin Carlsberg from Novo Nordisk] was added and the pH maintained at 7.5 under vigorous stirring by the controlled addition (pH-static) of 1.0N sodium hydroxide solution. After 33 h, 4.23 ml of 1.0N sodium hydroxide solution was consumed and the conversion degree was >99% (HPLC analysis). The reaction mixture was acidified to pH 2 with 32% hydrochloric acid, filtered over Decalite. After phase separation the aqueous phase was extracted with 3×275 ml ethyl acetate. The combined organic phases were dried on anhydrous sodium sulfate and evaporated. The residue was dissolved in dichloromethane, evaporated and dried at HV to give 1.56 g N-tert-butoxycarbonyl-3-(2-amino-4-bromophenylthio)-L-alanine as a pale yellow solid (yield: 99.8%).

EXAMPLE 3.3

Enzymatic Hydrolysis with Different Solvents (S)-3-(2-Amino-4-bromo-phenylsulfanyl)-2-tert-butoxycarbonylamino-propionic acid 100 mg (0.242 mmol) of N-tert-butoxycarbonyl-3-(2-amino-4-bromophenylthio)-L-alanine methyl ester (98%) was added to a system consisting of 20% organic co-solvent (see following table) and 80% buffer solution (0.1M sodium chloride; 3 mM sodium phosphate pH 7.5) under vigorous stirring. 100 ul Alcalase 2.4 L [a subtilisin Carlsberg from Novo Nordisk] was added and the pH maintained at 7.5 under vigorous stirring by the controlled addition (pH-static) of 0.1N sodium hydroxide solution. At the end of the reaction, the conversion degree was determined by HPLC.

| organic co-solvent, total reaction volume | conversion[a] in % | Comments |
|---|---|---|
| ethyl acetate, 20 ml | ~59% | Base consumption was exhausted (>200%) and the reaction was aborted. |
| THF, 50 ml | >97% | 24 mg (0.058 mmmol) substrate and 50 ul Alcalase |
| TBME, 25 ml | >99% | |

[a]The conversion was calculated from the peak area of HPLC analysis at 300 nm.

EXAMPLE 3.4

Enzymatic Hydrolysis with other Enzymes (S)-3-(2-Amino-4-bromo-phenylsulfanyl)-2-tert-butoxycarbonylamino-propionic acid 200 mg (0.493 mmol) of N-tert-butoxycarbonyl-3-(4-bromo-2-aminophenylthio)-L-alanine methyl ester (93.8%) was added to a system consisting of 5 ml TBME and 20 ml buffer solution (0.1M sodium chloride; 3 mM sodium phosphate pH 7.0) under vigorous stirring. Enzyme [see following table] was added and the pH maintained at 7.0 under vigorous stirring by the controlled addition (pH-static) of 0.1N sodium hydroxide solution. After termination of the reaction, the reaction mixture was washed twice with 25 ml TBME, acidified to pH 2.5 with 25% HCl and extracted with 3×25 ml ethyl acetate. The combined organic phases were dried over sodium sulfate, the solvent evaporated and the residue dried on a high vacuum.

| enzyme (company) | enzyme amount | time (h) | titrating agent consumed ml | product (amount; HPLC-purity) |
|---|---|---|---|---|
| Prozyme 6 (Amano Pharmaceuticals) | 42 mg | 44 | 4.76 | 191 mg; 92.2% |
| Savinase 16L (Novo Nordisk) | 100 µl | 43 | 4.969 | 195 mg: 90.7% |

EXAMPLE 4

(S)-(7-Bromo-4-oxo-2,3,4,5-tetrahydro-benzo[b][1,4]thiazepin-3-yl)-carbamic acid tert-butyl ester

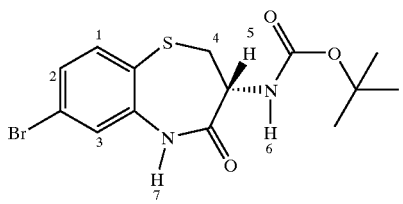

The reaction was carried out as described in G. C. Morton et al., Tet. Lett., 41 (2000) 3029–3033.). The product from the enzyme hydrolysis (15.2 g, 38.8 mmol, 1eq) and EDAC (1-Ethyl-3-(3-dimethylaminopropyl)carbodiimide hydrochloride) (7.44 g, 38.8 mmol, 1 eq) in DMF (500 mL) was stirred at room temperature for 16 h, concentrated and the residue dissolved in ethyl acetate (500 ml) and extracted with aq. NaHCO$_3$ (1M) (500 mL) and water (500 mL). Drying (with the use of Na$_2$SO$_4$) and concentrated to give the product (14.5 g, quantitative). Analytical data: $^1$H-NMR (CDCl$_3$, 400 MHz): 1.409 (s, 9H, O(CH$_3$)); 2.939 (t, 1H, H(4'), J=11.6 Hz); 3.794 (dd, 1H, H(4"), J$_{4"-5}$=11 Hz, J$_{4"-4'}$=6.4 Hz); 4.439 (m, 1H, H(5)); 5.567 (d, 1H, H(6), J$_{6-5}$=8 Hz); 7.306 (d, 1H, H(2), J$_{2-1}$=8 Hz, J$_{2-3}$=2 Hz); 7.337 (d, 1H, H(3), J$_{3-2}$=2 Hz); 7.748 (d, 1H, H(1), J$_{1-2}$=8 Hz); 8.042 (s, 1H, H(7)). IR: 3284 and 3184 cm$^{-1}$ (—NH); 1729 cm$^{-1}$ (Carbamate —C=O); 1678 cm$^{-1}$ (Amide —C=O); 1574 cm$^{-1}$ (Amide); 1251 cm$^{-1}$ (Ester). MS: m/z=373.3 [M+H$^+$] with $^{79}$Br; m/z=375.3 [M+H$^+$] with $^{81}$Br; m/z=395 [M+Na$^+$] with $^{79}$Br; m/z=397 [M+Na$^+$] with $^{81}$Br. Rf=0.23 in Ethyl acetate/Hexane 1:2 on SiO$_2$.

EXAMPLE 5

(S)-4-(2-tert-Butoxycarbonylamino-2-methoxycarbonyl-ethylsulfanyl)-3-nitro-benzoic acid allyl ester

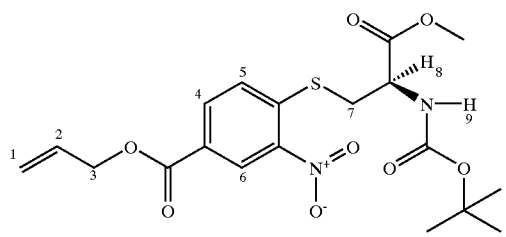

4-Fluoro-3-nitrobenzoic acid (49.95 g, 269.8 mmol, 1 eq) was dissolved in methanol (350 mL) and Cs$_2$CO$_3$ (44.06 g, 135.2 mmol, 0.5 eq) added and the solvent evaporated. Then the Cs-salt was dissolved in DMF, heated to 50° C. and treated with allylbromide (22.8 mL, 269.8 mmol, 1 eq). After 5 min, the solvent was evaporated and the resultant solid triturated in Et$_2$O. Filtration and evaporation gave the crude allylester quantitatively. The next step was carried according to M. K. Schwarz et al., J. Org. Chem. 1999, 64, 2219–2231. The allyl ester (30 g, 133.2 mmol, 1 eq), BOC-Cysteine-Methylester (31.35 g, 133.2 mmol, 1 eq) and DIPEA (68.3 mL, 399.6 mmol, 3 eq) was added slowly (exothermic reaction is observed) in EtOH and was stirred at room temperature for 3 hours, and concentrated to give a solid which was recrystallised from diisopropylether (46.16 g, 79%). Analaytical data: $^1$H-NMR (CDCl$_3$, 400 MHz): 1.443 (s, 9H, O(C$\underline{H}_3$)); 3.401 (dd, 1H, H(7'), $J_{7'-7''}$=2.4 Hz, $J_{7'-8}$=6 Hz); 3.506 (dd, 1H, H(7''), $J_{7''-7'}$=2.4 Hz, $J_{7''-8}$=6 Hz); 3.777 (s,3H, OC$\underline{H}_3$); 4.608 (m, 1H, H(8)); 4.860 (dt, 2H, H(3',3''), $J_{3-2}$=5.6 Hz; $J_{3-1}$=1.6 Hz); 5.322 (q, 1H, H(1'), J=0.8 Hz); 5.347 (t, 1H, H(1''), J=0.8 Hz); 5.406 (d, 1H, H(9), $J_{9-8}$=1.6 Hz); 6.032 (m, 1H, H(2)); 7.625 (d, 1H, H(5), $J_{5-4}$=8.4 Hz); 8.201 (dd, 1H, H(4), $J_{4-5}$=8.4 Hz, $J_{4-6}$=1.6 Hz); 8.830 (d, 1H, H(6), $J_{6-4}$=1.6 Hz). IR: 3350 cm$^{-1}$(—NH); 1742 cm$^{-1}$(Ester —C=O); 1719 cm$^{-1}$(Conj. Ester —C=O); 1686 cm$^{-1}$(Carbamate —C=O); 1523 and 1334 cm$^{-1}$(—NO$_2$); 1245 cm$^{-1}$(Ester). MS: m/z=441.3 [M+H$^+$]; m/z=458.4 [M+NH$_4^+$]; m/z=463.2 [M+Na$^+$].Rf=0.40 in Ethyl acetate/Hexane 1:2 on SiO$_2$.

EXAMPLE 6

(S)-3-Amino-4-(2-tert-butoxycarbonylamino-2-methoxycarbonyl-ethylsulfanyl)-benzoic acid allyl ester

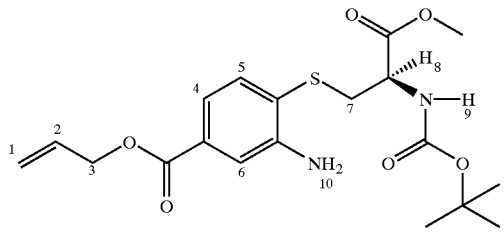

The reaction is carried out as described in J. Slade et.al., J. Med. Chem. 1985, 28, 1517–1521. The above product (506 mg, 1.15 mmol, 1 eq), aq. NH$_4$Cl (20 mL) and Zn (976 mg, 14.9 mmol, 13 eq) in DME (15 mL) was stirred and heated at 80° C. for 16 h. The solvent was evaporated and the residue dissolved in ethyl acetate (250 mL) and extracted with (aq.) sodium NaHCO$_3$ (1M) (3×50 mL). The organic phase was dried with NaSO$_4$ and evaporated to give a yellow oil which crystallized after few days (276 mg, 60%). Analytical data: $^1$H-NMR (CDCl$_3$, 400 MHz): 1.380 (s, 1H, O(C$\underline{H}_3$)); 3.283 (d, 2H, H(7',7''), $J_{7-8}$=4.4 Hz); 3.579 (s,3H, OC$\underline{H}_3$); 4.445 (s, 2H, H(10', 10'')); 4.554 (m, 1H, H(8)); 4.787 (ddd, 2H, H(2', 2''), J=1.2 Hz); 5.283 (dd, 1H, H(1'), $J_{1'-2}$=10.6 Hz, $J_{1'-1''}$=1.2 Hz); 5.390 (dd, 1H, H(1''), $J_{1''-2}$=17.8 Hz, $J_1''-1'$=1.2 Hz); 5.506 (d, 1H, H(9), $J_{9-8}$=7.6 Hz); 6.015 (m, 1H, H(8)); 7.360 (dd, 1H, H(2), $J_{4-5}$=8 Hz, $J_{4-6}$=1.6 Hz); 7.398 (d, 1H, H(6), $J_{6-4}$=1.6 Hz); 7.425 (d, 1H, H(5), $J_{5-4}$=8 Hz). IR: 3378cm$^{-1}$ (—NH, —NH$_2$); 1751 cm$^{-1}$(Ester —C=O); 1713 cm$^{-1}$(Conj. Ester —C=O); 1685 cm$^{-1}$(Carbamate —C=O); 1511 cm$^{-1}$(—Amide); 1220 cm$^{-1}$(Ester). MS: m/z=411.3 [M+H$^+$]; m/z=433.3 [M+Na$^+$]. Rf=;0.27 in Ethyl acetate/Hexane 1:2 on SiO$_2$.

EXAMPLE 7.1

Large Scale Enzymatic Hydrolysis (S)-3-Amino-4-(2-tert-butoxycarbonylamino-2-carboxy-ethylsulfanyl)-benzoic acid allyl ester

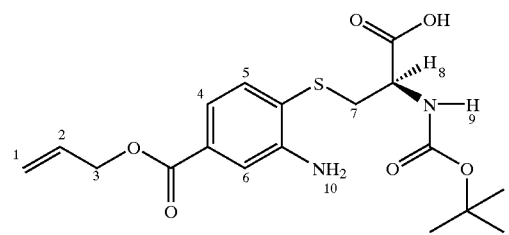

6.4 g (15.658 mmol) of N-tert-butoxycarbonyl-3-(4-alloxycarbonyl-2-aminophenylthio)-L-alanine methyl ester (99%) was dissolved in 480 ml TBME and emulsified in 1.5 L buffer solution (0.1M sodium chloride; 160 mM sodium phosphate pH 7.5) under vigorous stirring. 12.0 ml Alcalase 2.4 L [a subtilisin Carlsberg from Novo Nordisk] was added and the pH maintained at 7.5 under vigorous stirring by the controlled addition (pH-static) of 1.0N sodium hydroxide solution. After 48.5 h, 16.6 ml of 1.0N sodium hydroxide solution was consumed and the conversion degree was >97% (HPLC analysis). After phase separation, the aqueous phase was extracted once with 1 L TBME. The combined TBME phases were extracted with 2×0.4 L 0.1 M potassium phosphate buffer pH 7.6. The combined aqueous phases were acidified to pH 2 with 32% hydrochloric acid and extracted with 3×0.5 L ethyl acetate. In case a stabile emulsion was formed, the phase separation was achieved by filtration on Dicalite. The combined ethyl acetate phases were dried on anhydrous sodium sulfate and evaporated. The residue was dissolved in dichloromethane, evaporated and dried at HV to give 5.85 g N-tert-butoxycarbonyl-3-(4-alloxycarbonyl-2-aminophenylthio)-L-alanine as a yellow highly viscous oil (yield: 94.6%). Analytical data: $^1$H-NMR (DMSO, 400 MHz) 1.338 (s, 9H, OC(C$\underline{H}_3$)); 3.077 (dd, 1H, SC$\underline{H}_2$, J=12.8 Hz, J=6.8 Hz); 3.238 (dd, 1H, SC$\underline{H}_2$, J=13.8 Hz, J=4.6 Hz); 3.867 (m, 1H, COC$\underline{H}$NH); 4.753 (d, 2H, COOC$\underline{H}_2$, J=5.2 Hz); 5.526 (d, 1H, CH=C$\underline{H}_2$, J=10 Hz); 5.538 (d, 1H, CH=C$\underline{H}_2$, J=17.6 Hz); 5.595 (m, 2H, N$\underline{H}_2$); 6.018(ddtr, 1H, CH$_2$C$\underline{H}$=CH$_2$, J=16.6 Hz, J=10.6 Hz, J=5.6 Hz); 6.519 (m, 1H, CON$\underline{H}$CH); 6.876 (d, 1H, arom. CSC$\underline{H}$, J=8.4 Hz); 7.330 (d, 1H, arom. CSCHC$\underline{H}$, J=8.4 Hz); 7.338 (s, 1H, arom. C$\underline{H}$CNH$_2$). IR (ATR-IR) 3420 and 3355 cm$^{-1}$ (—NH, —NH2); 2980 and 2935 cm$^{-1}$ broad (—COOH); 1705 cm$^{-1}$ (COOH —C=O, carbamate —C=O); 1510 cm$^{-1}$ (amide —CO—NH); 1486 cm$^{-1}$ aromate; 1229 and 1160 cm$^{-1}$ (COOH); 982 and 932 cm$^{-1}$ (vinyl, —C=CH$_2$). MS (ESI-positive ionisation) m/z=397.1 [M+H$^+$]; m/z=419.4 [M+Na$^+$]. OR [α]$_D$=+16.16° (CHCl$_3$; c=1.0). HPLC analysis: column: ABZ+plus; mobile phase: A: 0.1% TFA in H$_2$0; B: MeCN; gradient B: 30–80% 0–15 min, 80–30% 15–16 min, 30% 16–19.5 min; flow; 1 ml/min; pressure:50–80 bar; detection: UV, 300 nm; retention times: 11.2 min (product-acid); 12.7 min (substrate-ester).

EXAMPLE 7.2

Small Scale Enzymatic Hydrolysis (S)-3-Amino-4-(2-tert-butoxycarbonylamino-2-car-boxy-ethylsulfanyl)-benzoic acid allyl ester 0.769 mg (1.658 mmol) of N-tert-butoxycarbonyl-3-(4-alloxycarbonyl-2-aminophenyl-thio)-L-alanine methyl ester was dissolved in 40 ml TBME and emulsified in 220 ml 0.1M sodium chloride solution; 3 mM sodium phosphate buffer pH 7.5 under vigorous stirring. 1.0 ml Alcalase 2.4 L [a subtilisin Carlsberg from Novo Nordisk] was added and the pH maintained at 7.5 under vigorous stirring by the controlled addition (pH-static) of 1.0N sodium hydroxide solution. After 45.4 h 23.6 ml of 1.0N sodium hydroxide solution was consumed and the conversion degree was >97% (HPLC analysis). The reaction mixture was extracted with 100 ml TBME. After phase separation, the aqueous phase was acidified to pH 2.3 with 32% hydrochloric acid and extracted with 3×250 ml ethyl acetate. In case a stabile emulsion was formed the phase separation was achieved by filtration on Dicalite. The combined ethyl acetate extracts were dried on anhydrous sodium sulfate and evaporated. The residue was dissolved in dichloromethane, evaporated and dried at HV to give 604 mg N-tert-butoxycarbonyl-3-(4-alloxycarbonyl-2-aminophenylthio)-L-alanine as a pale yellow solid (yield: 93.9%, purity: 95%).

EXAMPLE 7.3

Enzymatic Hydrolysis with Different Solvents (S)-3-Amino-4-(2-tert-butoxycarbonylamino-2-car-boxy-ethylsulfanyl)-benzoic acid allyl ester 200 mg (0.487 mmol) of N-tert-butoxycarbonyl-3-(4-alloxycarbonyl-2-aminophenylthio)-L-alanine methyl ester (96.7%) was added to a system consisting of 2 to 5 ml of an organic co-solvent (see following table) and 20 ml buffer solution (0.1M sodium chloride; 3 mM sodium phosphate pH 7.0) under vigorous stirring. Alcalase 2.4 L [a subtilisin Carlsberg from Novo Nordisk, amount see following table] was added and the pH maintained at 7.0 under vigorous stirring by the controlled addition (pH-static) of 0.1N sodium hydroxide solution. The reaction was monitored by the consumption of titrating agent, and the formation of the product confirmed by HPLC.

| organic co-solvent, amount | Alcalase, amount | Time (h) | comments |
|---|---|---|---|
| ethanol, 2.0 ml | 100 µl | 72 | consumption of titrating agent at the end of the reaction: 115% |
| acetone, 5.0 ml | 200 µl | 171 | consumption of titrating agent at the end of the reaction: 103% |
| THF, 5.0 ml | 100 µl | 146 | consumption of titrating agent at the end of the reaction: 98% |
| TBME, 5.0 ml | 100 µl | 72 | consumption of titrating agent at the end of the reaction: 119% |

EXAMPLE 7.4

Enzymatic Hydrolysis with other Enzymes (S)-3-Amino-4-(2-tert-butoxycarbonylamino-2-car-boxy-ethylsulfanyl)-benzoic acid allyl ester 200 mg (0.487 mmol) of N-tert-butoxycarbonyl-3-(4-alloxycarbonyl-2-aminophenylthio)-L-alanine methyl ester (96.7%) was added to a system consisting of 5 ml TBME and 20 ml buffer solution (0.1M sodium chloride; 3 mM sodium phosphate pH 7.0) under vigorous stirring. Enzyme [see following table] was added and the pH maintained at 7.0 under vigorous stirring by the controlled addition (pH-static) of 0.1N sodium hydroxide solution. The reaction was monitored by the consumption of titrating agent, and the formation of the product confirmed by HPLC.

| enzyme (company) | enzyme amount | Time H | comments |
|---|---|---|---|
| Prozyme 6 (Amano Pharmaceuticals) | 50 mg | 42 | consumption of titrating agent at the end of the reaction: 112% |
| Proteinase K (Fluka) | 25 mg | 137 | slow: after 137 h only 40% (of theory) of titrating agent was consumed |

EXAMPLE 7.5

Enzymatic Hydrolysis at Higher Temperature (S)-3-Amino-4-(2-tert-butoxycarbonylamino-2-car-boxy-ethylsulfanyl)-benzoic acid allyl ester 200 mg (0.487 mmol) of N-tert-butoxycarbonyl-3-(4-alloxycarbonyl-2-aminophenylthio)-L-alanine methyl ester (96.7%) was added to a system consisting of 5 ml TBME and 20 ml buffer solution (0.1M sodium chloride; 3 mM sodium phosphate pH 7.0) under vigorous stirring at 40° C. 100 µl of Alcalase 2.4 L [a subtilisin Carlsberg from Novo Nordisk] was added and the pH maintained at 7.0 under vigorous stirring at 40° C. by the controlled addition (pH-static) of 0.1N sodium hydroxide solution. After a consumption 5.44 ml of titrating agent (112% of theory; after 17.4 h), the reaction mixture was washed with 25 ml TBME, acidified to pH 2.5 with 1N HCl and extracted with 3×25 ml ethyl acetate. The combined organic phases were dried over sodium sulfate, the solvent evaporated and the residue dried on a high vacuum to give 190 mg (0.479 mmol; 98%) of the product acid in 94.5% HPLC-purity (area-%).

EXAMPLE 8

(S)-3-tert-Butoxycarbonylamino-4-oxo-2,3,4,5-tet-rahydro-benzo[b][1,4]thiazepine-7-carboxylic acid allyl ester

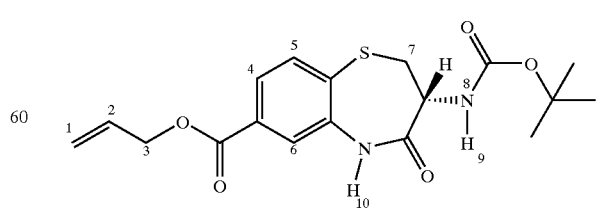

The reaction is carried out as described in G. C. Morton et al., Tet. Lett., 41 (2000) 3029–3033. The product from the enzyme hydrolysis (5.6 g, 14.1 mmol, 1 eq) was dissolved in DMF (75 mL) and treated with EDAC (2.70 g, 14.1 mmol, 1 eq) and stirred at room temperature for 16 h. The residue was then dissolved in ethyl acetate (500 mL) and extracted with (aq.) NaHCO$_3$ (1M) (3×150 mL) and water (3×150 mL). The organic phase was dried (Na$_2$SO$_4$) and evaporated to give yellow oil. After chromatography with ethyl acetate/hexane 1:2. Yellow crystals were obtained (4.96 g, 93%). Analytical data: $^1$H-NMR (CDCl$_3$, 400 MHz): 1.400 (s, 1H, O(CH$_3$)); 3.014 (t, 1H, H(7' or 7"), J=12 Hz); 3.815 (dd, 1H, H(7' or 7"), J$_{7-8}$=12 Hz, J$_{7'-7"}$=6.4 Hz); 4.466 (m, 1H, H(8)); 4.835 (d, 2H, H(3', 3"), J$_{3-2}$=5.7 Hz); 5.316 (dd, 1H, H(1'), J$_{1'-2}$=10.5 Hz, J$_{1'-1"}$=1.2 Hz); 5.413 (dd, 1H, H(1"), J$_{1"-2}$=17.2 Hz, J$_{1"-1'}$=1.2 Hz); 5.581 (d, 1H, H(9), J$_{9-8}$=8 Hz); 6.013 (m, 1H, H(8)); 7.338 (d, 1H, H(5), J$_{5-4}$=11.1 Hz); 7.704 (s, 1H, H(10)); 7.751 (d, 1H, H(6), J$_{6-4}$=1.8 Hz);7.338 (dd, 1H, H(2), J$_{4-5}$=11.1 Hz, J$_{4-6}$=1.8 Hz). IR: 3206 cm$^{-1}$ (—NH); 1720 cm$^{-1}$ (Carbamate —C=O); 1671 cm$^{-1}$ (Amide —C=O); 1500 cm$^{-1}$ (Amide —CO—NH); 1209 cm$^{-1}$ (Ester). MS: m/z=379.3 [M+H$^+$]; m/z=401.4 [M+Na$^+$]. Rf=0.36 in Ethyl acetate/Hexane 1:2 on SiO$_2$.

EXAMPLE 9

(S)-3-Amino-4-(2-tert-butoxycarbonylamino-2-carboxy-ethylsulfanyl)-benzoic acid

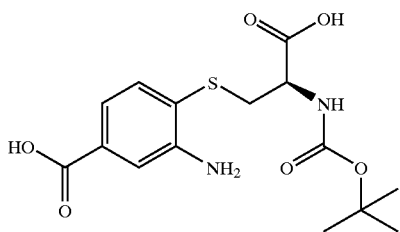

200 mg (0.540 mmol) of N-tert-butoxycarbonyl-3-(4-carboxy-2-aminophenylthio)-L-alanine methyl ester was added to a system consisting of 5 ml TBME and 20 ml buffer solution (0.1M sodium chloride; 3 mM sodium phosphate pH 7.0) under vigorous stirring. 100 µl of Alcalase 2.5 L [a subtilisin Carlsberg from Novo Nordisk] was added and the pH maintained at 7.0 under vigorous stirring by the controlled addition (pH-static) of 0.1N sodium hydroxide solution. After a consumption 5.847 ml of titrating agent (108% of theory; after 1.5 h) the reaction mixture was washed twice with 25 ml TBME, acidified to pH 2.5 with 25% HCl and extracted with 3×25 ml ethyl acetate. The combined organic phases were dried over sodium sulfate, the solvent evaporated and the residue dried on a HV to give 187 mg (0.479 mmol) N-tert-butoxycarbonyl-3-(2-amino-4-carboxyphenylthio)-L-alanine as yellow crystals (yield: 93.4%). Analytical data: HPLC-purity: 96.4%% (area). $^1$H-NMR (DMSO, 400 MHz) 1.378 (s, 9H, OC(CH$_3$)); 2.982 (dd, 1H, SCH$_2$, J=13.2 Hz, J=9.6 Hz); 3.150 (dd, 1H, SCH$_2$, J=13.2 Hz, J=4.4 Hz); 3.950 (m, 1H, COCHNH); 5.542 (m, 2H, —NH$_2$); 7.067 (dd, 1H, CONHCH, J=8.0 Hz, J=1.6 Hz); 7.201 (d, 1H, arom. SCCH, J=8.0 Hz); 7.298 (d, 1H, arom. SCCHCH, J=8.0 Hz); 7.323 (d, 1H, arom. CHCNH$_2$, J=1.6 Hz); 12.73 (bs, 2H, 2 —COOH). IR: 3445 and 3347 cm$^{-1}$ (—NH, —NH2); 2977 and 2930 cm$^{-1}$ broad (—COOH); 1720 and 1692 cm$^{-1}$ (COOH —C=O, carbamate —C=O); 1608 cm$^{-1}$ (—COO$^-$); 1509 cm$^{-1}$ (amide —CO—NH); 1486 cm$^{-1}$ (aromate); 1247 and 1163 cm$^{-1}$ (COOH). ISN-MS: m/z=355.1 [M−H$^+$]. OR [α]$_D$=+13.00° (EtOH; c=1.0).

What is claimed is:

1. A process for preparing a compound of formula I

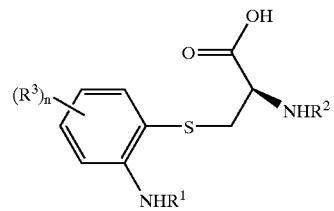

wherein

R$^1$ is hydrogen or alkyl;

R$^2$ is an amino protecting group;

each R$^3$ is independently from each other a halogen, carboxyl, alkoxycarbonyl, alkenyloxycarbonyl or benzyloxycarbonyl; and n is 1 or 2, the process comprising:

reacting a compound of formula II

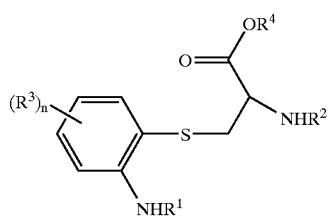

wherein R$^1$, R$^2$, R$^3$ and n are as defined above and

R$^4$ is alkyl or benzyl, a with a protease in an aqueous system containing an organic co-solvent and b. recovering the produced product.

2. The process according to claim 1, wherein

R$^1$ is hydrogen or alkyl;

R$^2$ is an amino protecting group;

each R$^3$ is independently from each other a halogen, carboxyl or alkenyloxycarbonyl;

R$^4$ is alkyl or benzyl; and n is 1 or 2.

3. The process according to claim 1, wherein

R$^1$ is hydrogen;

R$^2$ is an amino protecting group;

R$^3$ is halogen, carboxyl or alkenyloxycarbonyl;

R$^4$ is alkyl; and n is 1.

4. The process according to claim 1, wherein the reaction is carried out at pH of 6.0–8.5.

5. The process according to claim 1, wherein the protease is selected from the group consisting of *Bacillus* protease, subtilisin, *Aspergillus* protease and *Tritachium* protease.

6. The process according to claim 1, wherein the organic co-solvent is selected from the group consisting of tetrahydrofuran, dioxan, tert-butyl methyl ether, $C_{1-8}$-alkohol, ethyl acetate, dimethylsulfoxide, dimethylacetamide and acetone.

7. The process according to claim 1, further comprising cyclizing the compound of formula I to a benzothiazepine of formula III

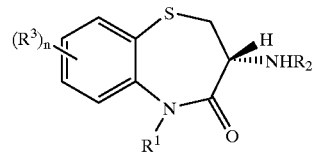

wherein $R^1$, $R^2$, $R^3$, $R^4$ and n are as described for compounds of formula I and II.

* * * * *